United States Patent [19]

Stemp et al.

[11] Patent Number: 5,053,427

[45] Date of Patent: Oct. 1, 1991

[54] GUANIDINO-SUBSTITUTED BENZOPYRANS AND THEIR USE AS PHARMACEUTICALS

[75] Inventors: Geoffrey Stemp; Gordon Burrell, both of Harlow; David G. Smith, Epsom, all of England

[73] Assignee: Beecham Group p.l.c., England

[21] Appl. No.: 407,227

[22] Filed: Sep. 14, 1989

[30] Foreign Application Priority Data

Sep. 16, 1988 [GB] United Kingdom ................ 8821826
Apr. 1, 1989 [GB] United Kingdom ................ 8907394
Jul. 28, 1989 [GB] United Kingdom ................ 8917176

[51] Int. Cl.$^5$ ................ C07D 311/04; A61K 31/35
[52] U.S. Cl. ................ 514/456; 549/399; 549/404
[58] Field of Search ................ 549/399, 404; 514/456

[56] References Cited

U.S. PATENT DOCUMENTS 4,088,785  5/1978  Diamond et al. .................... 514/595

FOREIGN PATENT DOCUMENTS 0126367 11/1984 European Pat. Off. ............ 549/399
0168619  1/1986 European Pat. Off. ............ 548/486
0205292 12/1986 European Pat. Off. ............ 546/115
0344747 12/1989 European Pat. Off. ............ 514/456
2019400 10/1979 United Kingdom ................ 564/57

OTHER PUBLICATIONS

Patent Abstracts of Japan, vol. 9, No. 134 (C-285) (1857) Jun. 8, 1985.
Journal of Medicinal Chemistry, vol. 21, No. 8, 1978, pp. 773-781.

Primary Examiner—Alan L. Rotman
Attorney, Agent, or Firm—Rosenman & Colin

[57] ABSTRACT

Compounds of formula (I) and pharmaceutically acceptable salts thereof:

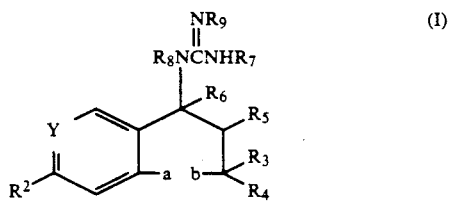

(I)

wherein
a and b together form an —O— or —CH$_2$— linkage or a bond;
either Y is N and R$_2$ is hydrogen; or
Y is C-R$_1$
wherein
either one of R$_1$ and R$_2$ is hydrogen and the other is nitro, cyano, halo, CF$_3$, formyl, aldoxime, CF$_3$O, NO$_2$—CH=CH—, NC—CH=CH—; a group R$_x$X— wherein R$_x$ and C$_{1-6}$ alkyl, aryl or heteroaryl either of which may be optionally substituted by one, two or three of C$_{1-4}$ alkyl, C$_{1-4}$ alkoxy, nitro, halo, CF$_3$ and cyano; and X is C=O, O.C=O, C=O.O, CHOH, SO, SO$_2$, O.SO, O.SO$_2$, CONH, O.CONH, C=S, O.C=S, C=S.O, CH.SH, SONH, SO$_2$NH, O.SONH, O.SO$_2$NH, CO—CH=CH, C=NHOH, C=NNH$_2$; or a group R$_y$R$_z$NZ— wherein R$_y$ and R$_z$ are independently hydrogen or C$_{1-6}$ alkyl and Z is C=O, SO or SO$_2$; or
R$_1$ is a C$_{3-8}$ cycloalkyl group or a C$_{1-6}$ alkyl group optionally substituted by a group which is hydroxy, C$_{1-6}$ alkoxy, amino optionally substituted by one or two C$_{1-6}$ alkyl groups, C$_{1-7}$ alkanoylamino, C$_{3-8}$ cycloalkyloxy or C$_{3-8}$ cycloalkylamino; and R$_2$ is hydrogen; or
one of R$_1$ and R$_2$ is nitro, cyano or C$_{1-3}$ alkylcarbonyl and the other is a different group selected from nitro, cyano, halo, C$_{1-3}$ alkylcarbonyl, methoxy or amino optionally substituted by one or two C$_{1-6}$ alkyl or by C$_{2-7}$ alkanoyl;
either one of R$_3$ and R$_4$ is hydrogen or C$_{1-4}$ alkyl and the other is C$_{1-4}$ alkyl; or
R$_3$ and R$_4$ together are C$_{2-5}$ polymethylene;
either R$_5$ is hydrogen, hydroxy, C$_{1-6}$ alkoxy or C$_{1-7}$ acyloxy; and
R$_6$ is hydrogen; or
R$_5$ and R$_6$ together are a bond;
either R$_7$ is hydrogen, C$_{1-6}$ alkyl, C$_{3-6}$ cycloalkyl, C$_{2-6}$ alkenyl or C$_{2-6}$ alkynyl; and
R$_8$ is hydrogen or C$_{1-6}$ alkyl; or
R$_7$ and R$_8$ together are C$_{2-4}$ polymethylene;
R$_9$ is CN, NO$_2$, COR$_{10}$ or SO$_2$R$_{10}$ wherein R$_{10}$ is C$_{1-3}$ alkyl, NH$_2$, NH(C$_{1-3}$ alkyl), CF$_3$ or phenyl optionally substituted as defined for R$_x$; and
the R$_8$N(NR$_9$)NHR$_7$ moiety is trans to the R$_5$ group when R$_5$ is hydroxy, C$_{1-6}$ alkoxy or C$_{1-7}$ acyloxy;
having antihypertensive and/or bronchodilator activity, processes for their preparation and their use as pharmaceuticals.

12 Claims, No Drawings

GUANIDINO-SUBSTITUTED BENZOPYRANS AND THEIR USE AS PHARMACEUTICALS

This invention relates to novel compounds having pharmacological activity, to a process for their preparation and to their use as pharmaceuticals.

EP-A-107423, EP-A-168619, EP-A-126367, EP-A-205292 and EP-A-321175 (Beecham Group p.l.c.), corresponding to U.S. Pat. Nos. 4,496,565, 4,800,212, 4,575,511 and 4,812,459 respectively, describe benzopyran, tetrahydronaphthalene, pyranopyridine and indane derivatives having inter alia a ureido substituent at the 4-position and possessing pharmacological activity, in particular, antihypertensive activity and/or bronchodilator activity.

A novel group of compounds has now been discovered, which compounds have a guanidine substituent at the 4-position. These compounds have been found to have blood pressure lowering activity, useful in the treatment of hypertension, and bronchodilator activity, useful in the treatment of respiratory tract disorders. In addition, these compounds are believed to be $K^+$ channel activators which indicates that they are of potential use in the treatment of disorders associated with smooth muscle contraction of the gastro-intestinal tract, respiratory system, uterus or urinary tract including the ureter. Such disorders include irritable bowel syndrome and diverticular disease; reversible airways obstruction including asthma; premature labour; and incontinence, renal cholic and disorders associated with kidney stones. They are also indicated as of potential use in the treatment of cardiovascular disorders other than hypertension, such as congestive heart failure, angina, peripheral vascular disease, cerebral vascular disease, pulmonary hypertension and right heart failure.

Accordingly, the present invention provides a compound of formula (I) or a pharmaceutically acceptable salt thereof:

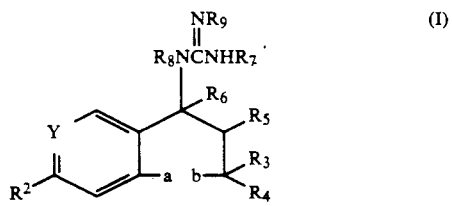

(I)

wherein
a and b together form an —O— or —CH$_2$— linkage or a bond;
either Y is N and R$_2$ is hydrogen; or
Y is C-R$_1$
wherein
either one of R$_1$ and R$_2$ is hydrogen and the other is nitro, cyano, halo, CF$_3$, formyl, aldoxime, CF$_3$O, NO$_2$—CH=CH—, NC—CH=CH—; a group R$_x$X— wherein R$_x$ is C$_{1-6}$ alkyl, aryl or heteroaryl either of which may be optionally substituted by one, two or three of C$_{1-4}$ alkyl, C$_{1-4}$ alkoxy, nitro, halo, CF$_3$ and cyano; and X is C=O, O.C=O, C=O.O, CHOH, SO, SO$_2$, O.SO, O.SO$_2$, CONH, O.CONH, C=S, O.C=S, C=S.O, CH.SH, SONH, SO$_2$NH, O.SONH, O.SO$_2$NH, CO—CH=CH, C=NHOH, C=NNH$_2$; or a group R$_y$R$_z$NZ— wherein R$_y$ and R$_z$ are independently hydrogen or C$_{1-6}$ alkyl and Z is C=O, SO or SO$_2$; or R$_1$ is a C$_{3-8}$ cycloalkyl group or a C$_{1-6}$ alkyl group optionally substituted by a group which is hydroxy, C$_{1-6}$ alkoxy, amino optionally substituted by one or two C$_{1-6}$ alkyl groups, C$_{1-7}$ alkanoylamino, C$_{3-8}$ cycloalkyloxy or C$_{3-8}$ cycloalkylamino; and R$_2$ is hydrogen; or one of R$_1$ and R$_2$ is nitro, cyano or C$_{1-3}$ alkylcarbonyl and the other is a different group selected from nitro, cyano, halo, C$_{1-3}$ alkylcarbonyl, methoxy or amino optionally substituted by one or two C$_{1-6}$ alkyl or by C$_{2-7}$ alkanoyl;

either one of R$_3$ and R$_4$ is hydrogen or C$_{1-4}$ alkyl and the other is C$_{1-4}$ alkyl; or R$_3$ and R$_4$ together are C$_{2-5}$ polymethylene;

either R$_5$ is hydrogen, hydroxy, C$_{1-6}$ alkoxy or C$_{1-7}$ acyloxy; and

R$_6$ is hydrogen; or

R$_5$ and R$_6$ together are a bond;

either R$_7$ is hydrogen, C$_{1-6}$ alkyl, C$_{3-6}$ cycloalkyl, C$_{2-6}$ alkenyl or C$_{2-6}$ alkynyl; and R$_8$ is hydrogen or C$_{1-6}$ alkyl; or R$_7$ and R$_8$ together are C$_{2-4}$ polymethylene;

R$_9$ is CN, NO$_2$, COR$_{10}$ or SO$_2$R$_{10}$ wherein R$_{10}$ is C$_{1-3}$ alkyl, NH$_2$, NH(C$_{1-3}$ alkyl), CF$_3$ or phenyl optionally substituted as defined for Rx; and the R$_8$N(NR$_9$)NHR$_7$ moiety is trans to the R$_5$ group when R$_5$ is hydroxy, C$_{1-6}$ alkoxy or C$_{1-7}$ acyloxy.

Preferably Y is N or C-R$_1$ and a and b together are an —O— linkage or Y is C-R$_1$ and a and b together are a bond.

When either one of R$_1$ and R$_2$ is hydrogen, the other is preferably selected from halo, CF$_3$, C$_{1-6}$ alkylcarbonyl, C$_{1-6}$ alkoxycarbonyl, nitro or cyano.

When one of R$_1$ and R$_2$ is nitro, cyano or C$_{1-3}$ alkylcarbonyl the other is, favourably, amino optionally substituted by one or two C$_{1-6}$ alkyl groups or by C$_{2-7}$ alkanoyl. In particular, when one of R$_1$ and R$_2$ is nitro, cyano or acetyl, the other is amino, methylamino, dimethylamino or acetylamino. Preferably, when one of R$_1$ and R$_2$ is nitro or cyano, especially cyano, the other is amino.

Halo substituents in R$_1$ and/or R$_2$ are usually chloro or bromo.

Values for R$_x$ when alkyl in R$_1$/R$_2$ are usually selected from methyl, ethyl, n- and iso-propyl, n-, iso-, sec- and tert-butyl preferably methyl or ethyl. Suitable examples of other alkyl or alkyl containing groups in R$_1$ and in R$_3$ and R$_4$ when alkyl include those listed for R$_1$ and R$_2$ alkyl containing groups. C$_{3-8}$ cycloalkyl includes C$_3$, C$_4$, C$_5$, C$_6$ cycloalkyl, in particular, cyclopentyl.

A sub-group of R$_x$ heteroaryl is 5- or 6-membered monocyclic or 9- or 10-membered bicyclic heteroaryl of which 5- or 6-membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different. Examples of 5- or 6-membered monocyclic heteroaryl containing one, two or three heteroatoms which are selected from the class of oxygen, nitrogen and sulphur include furyl, thienyl, pyrryl, oxazolyl, thiazolyl, imidazolyl and thiadiazolyl, and pyridyl, pyridazyl, pyrimidyl, pyrazyl and triazyl. Preferred examples of such groups include furanyl, thienyl, pyrryl and pyridyl, in particular 2- and 3-furyl, 2- and 3-pyrryl, 2- and 3-thienyl, and 2-, 3- and 4-pyridyl. Examples of 9- or 10-membered bicyclic heteroaryl containing one, two or three heteroatoms which are selected from the class of oxygen, nitrogen and sulphur include benzofuranyl, benzothienyl, indolyl and indazolyl, quinolyl and isoquinolyl, and quinazolinyl. Preferred examples of such groups include 2- and 3-benzofuryl, 2- and 3-benzothienyl, and 2- and 3-indolyl, and 2- and 3-quinolyl.

Preferred examples of the groups or atoms for optional substitution of $R_x$ when aryl or heteroaryl include methyl, methoxy, hydroxy, chloro, nitro or cyano.

$R_1$ is preferably nitro, cyano, acetyl, $CF_3$, methyl, ethyl, isopropyl, t-butyl or cyclopentyl.

Preferably $R_3$ and $R_4$ are both methyl groups.

Suitable examples of $R_5$ when alkoxy include methoxy, ethoxy, n- and iso-propoxy, of which methoxy is preferred. When $R_5$ is $C_{1-7}$ acyloxy it is usually $C_{1-7}$ carboxylic acyloxy, such as $C_{1-7}$ alkanoyloxy wherein the alkyl moiety is usually as listed for alkyl in $R_1$ and $R_2$ above.

$R_5$ is preferably hydroxy, or $R_5$ and $R_6$ together are a bond.

Suitable values for $R_7$ and $R_8$ when $C_{1-6}$ alkyl/$C_{3-6}$ cycloalkyl include those values described for $R_1$ and $R_2$ alkyl moieties.

Examples of $R_7$ when alkenyl and alkynyl include vinyl, prop-2-enyl, 1-methylvinyl, but-1-enyl, but-2-enyl, but-3-enyl, 1-methylenepropyl, 1-methylprop-1-enyl and 1-methylprop-2-enyl in their E and Z forms where stereoisomerism exists; and the corresponding alkynyl analogues where appropriate of the above.

When $R_7$ and $R_8$ are joined, they are favourably $-(CH_2)_2-$.

Favourably $R_7$ is hydrogen, methyl, $-CH-CH=CH_2$, $CH_2C\equiv CH$ or cyclopropyl, preferably methyl, and $R_8$ is hydrogen.

Suitable values for $R_{10}$ in $R_9$ are as described for $R_1$ when $C_{1-3}$ alkyl, and when $R_{10}$ is substituted phenyl, suitable substituents are as described for $R_x$ when aryl. $R_9$ is preferably cyano.

Examples of pharmaceutically acceptable salts include acid addition salts with acids such as hydrochloric, hydrobromic, phosphoric, sulphuric, citric, tartaric, lactic or acetic acid.

The compounds of formula (I) wherein $R_5$ and $R_6$ do not from a bond, have at least one asymmetric centre and therefore exist in more than stereoisomeric form. The invention extends to each of these forms individually and to mixtures thereof, such as racemates.

The compounds of formula (I) and their salts may form solvates, such as hydrates, and these are included as part of the invention, wherever a compound of formula (I) or a salt thereof is herein referred to.

A preferred group of compounds within formula (I) is of formula (II):

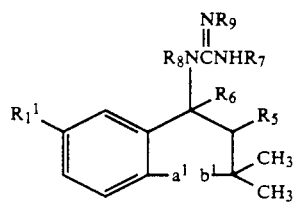

(II)

wherein $R_1^1$ is nitro, cyano, $CF_3$, methyl, ethyl, isopropyl or acetyl, $a^1$ and $b^1$ together form an $-O-$ linkage or a bond; and R5 to . 9 are as defined in formula (I).

Suitable and preferred values for the variables are as described for the corresponding variables in formula (I).

The present invention also provides a process for the preparation of a compound of formula (I) wherein $R_7$ is other than hydrogen and $R_9$ is CN or $SO_2NH_2$, which process comprises the reaction of a compound of formula (III):

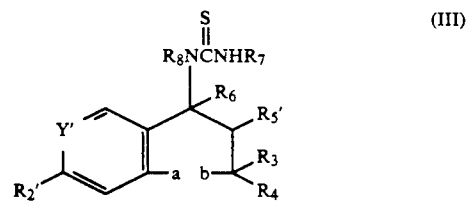

(III)

with phosgene ($COCl_2$) and either i) when $R_9$ is CN, with cyanamide or ii) when $R_9$ is $SO_2NH_2$, with sulfamide; wherein $Y'$ and $R_2'$ are Y and $R_2$ respectively or moieties convertible thereto; $R_5$ is protected hydroxy or $R_5$ other than hydroxy; and the remaining variables are as defined in formula (I); and thereafter optionally converting $Y'$, $R_2$ and/or $R_5'$ to Y, $R_2$ and $R_5$ as desired or necessary; optionally converting a compound wherein $R_6$ forms a bond to R6 is hydrogen; and thereafter optionally forming a pharmaceutically acceptable salt thereof.

The reaction preferably takes place in an inert solvent, such as tetrahydrofuran, at $-10°$ to $+25°$ C., preferably around $0°$ C. to ambient, in an inert atmosphere, for example, under nitrogen, preferably in the presence of a base, such as diisopropylethylamine.

The reaction proceeds via intermediates of formula (IVa) and/or (IVb):

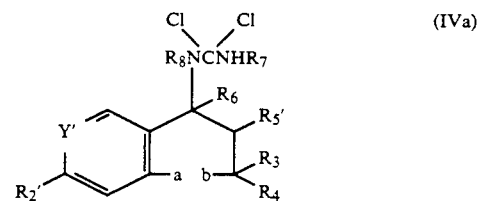

(IVa)

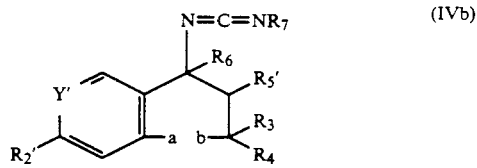

(IVb)

Alternative methods of forming compounds of formula (I) are as described in J.Med.Chem. 1978 Vol 21 p773-781.

$R_5'$ is usually acetoxy, when $R_5$ in the desired compound of formula (I) is hydroxy. It may be converted to $R_5$ is hydroxy by hydrolysis in an alkanol solvent such as methanol in the presence of a base such as potassium carbonate.

Conversions of $Y'$ to Y and $R_2'$ to $R_2$ are conventional in the art of aromatic chemistry.

Compounds wherein $R_5$ and $R_6$ together are a bond, and compounds wherein $R_5$ and $R_6$ are both hydrogen, may be prepared according to the methods described in the aforementioned patent publications, although when $R_5$ and $R_6$ are hydrogen, the process described hereinafter, from an intermediate of formula (VII), is generally preferred.

Pharmaceutically acceptable salts may be formed conventionally.

Intermediates of formula (III) are described in EP-A-107423, EP-A-168619, EP-A-126367, EP-A-205292 and EP-A-321175.

The invention also provides an alternative process for the preparation of compounds wherein $R_7$ and $R_8$ together are $C_{2-4}$ polymethylene, which process comprises the reaction of dimethyl N-cyanodithioiminocarbonate with a compound of formula (V):

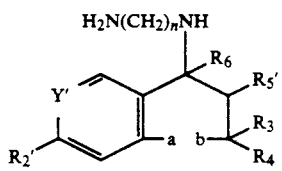

wherein n is 2, 3 or 4 and the remaining variables are as hereinbefore defined; and thereafter optionally converting Y', $R_2'$ and/or $R_5'$ to Y, $R_2$ and $R_5$ as desired or necessary; and thereafter optionally forming a pharmaceutically acceptable salt thereof.

The reaction takes place at elevated temperatures, preferably at reflux temperatures, in an inert solvent, such as toluene.

Conversions of Y', $R_2$, $R_5$, $R_6$ and formation of salts may be carried out as hereinbefore described for the process utilising intermediates of formula (III).

Intermediates of formula (V) where R5 is hydroxy may be prepared from the epoxide of formula (VI):

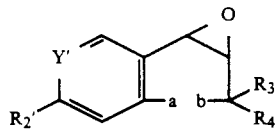

by reaction with $H_2N(CH_2)_nNH_2$ according to the method described in Description 7 hereinafter.

Intermediates of formula (V) wherein $R_5'$ is hydrogen may be prepared from intermediates of formula (XI) defined hereinafter, by reaction with $H_2N(CH_2)_nNH_2$.

Intermediates of the formula (VI) are known or prepared by analogous methods to those used for structurally similar compounds, for example as described in U.S. Pat. Nos. 4,758,677, 4,446,113, 4,542,149, 4,800,212 and 4,181,2459 (Evans et. al.) and EP-A-205292, 214818, 250077 and 321175 (Beecham Group p.l.c.).

A further process for the preparation of a compound of formula (I) wherein $R_7$ and $R_8$ are not joined together, comprises reacting a compound of formula (VII):

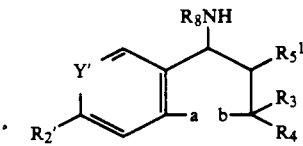

wherein the $R_8NH$ and $R_5^1$ groups are trans when $R_5^1$ is OH, with a compound of formula (VIII):

wherein $R_5^1$ is hydroxy or hydrogen, L is a leaving group and E is a leaving group or $NHR_7$ as defined, and the remaining variables are as hereinbefore defined; and thereafter, when E is a leaving group, reacting the resulting compound with $R_7NH_2$; and optionally converting $R_9$ to other $R_9$ and/or Y' and/or $R_2'$ to Y and/or $R_2$ as desired or necessary; optionally converting an $R_5^1$ hydroxy group to other $R_5$ or to a compound wherein $R_5$ and $R_6$ together are a bond; and thereafter optionally forming a pharmaceutically acceptable salt thereof.

Suitable values for E when a leaving group and L, include $SCH_3$, chloro, $C_{1-6}$ alkoxy or phenoxy, preferably $SCH_3$.

The reaction preferably takes place in an inert solvent, such as acetonitrile, preferably at elevated temperatures.

Preferably E is $SCH_3$, in which case the resulting compound of formula (IX):

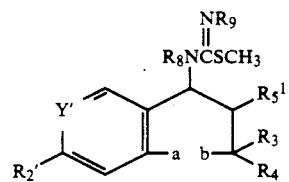

may be converted to a corresponding compound of formula (I) by reaction with $R_7NH_2$ under conventional conditions. When $R_7$ is hydrogen, aqueous ammonia solution/pyridine may be used, at ambient temperature.

When $R_9$ is cyano, it may be converted to $CONH_2$ by conventional acid hydrolysis.

Conversions of Y' and $R_2'$ and formation of salts may be carried out as hereinbefore described for the process utilising intermediates of formula (III).

Conversion of $R_5/R_6$ may be carried out as described in the aforementioned European Patent Publications.

Intermediates of the formula (VII) wherein $R_5^1$ is hydroxy are known and may be prepared according to the methods described in the aforementioned Patent Publications.

Intermediates of formula (VII) wherein $R_5^1$ is hydrogen, and $R_8$ is hydrogen may be prepared from intermediates of formula (X) according to the following reaction scheme:

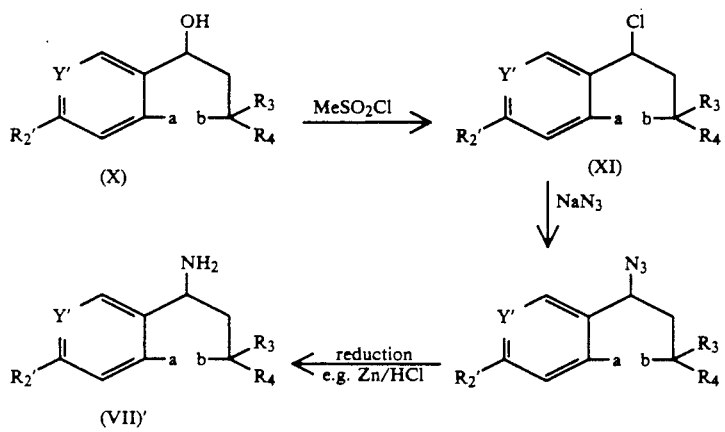

Intermediates of the formula (VII) wherein $R_8$ is $C_{1-6}$ alkyl and $R_5^1$ is hydrogen may be prepared from intermediates of formula (VII) by convential amine alkylation or reductive amination methods.

It will be appreciated that, when $R_5$ is hydroxy, $C_{1-6}$ alkoxy or $C_{1-7}$ acyloxy, it is preferred that the compound of formula (I) is isolated in the form of a pure single enantiomer, preferably the (3S,4R)-isomer. This may either be prepared by resolution or stereospecifically using resolved intermediates.

As mentioned previously, the compounds of formula (I) have been found to have blood-pressure lowering activity. They are therefore useful in the treatment of hypertension. They are also believed to be of potential use in the treatment of other disorders hereinbefore referred to.

The present invention accordingly provides a pharmaceutical composition which comprises a compound of formula (I) or a pharmaceutically acceptable salt thereof, and a pharmaceutically acceptable carrier. In particular, the present invention provides an anti-hypertensive or bronchodilator pharmaceutical composition which comprises an effective amount of a compound of formula (I) or a pharmaceutically acceptable salt thereof, and a pharmaceutically acceptable carrier.

The compositions are preferably adapted for oral administration. However, they may be adapted for other modes of administration, for example parenteral administration for patients suffering from heart failure. Other alternative modes of administration include sublingual or transdermal administration. A composition may be in the form of spray, aerosol or other conventional method of inhalation, for treating respiratory tract disorders.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art.

The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The present invention further provides a method of prophylaxis or treatment of hypertension or respiratory tract disorders in mammals including man, which comprises administering to the suffering mammal an effective amount of a compound of formula (I) or a pharmaceutically acceptable salt thereof.

An effective amount will depend on the relative efficacy of the compound, the severity and nature of the disorder being treated and the weight of the sufferer. However, a unit dose form of a composition of the invention may contain from 0.05 to 500 mg of a compound of the invention and more usually from 0.1 to 50 mg, for example 0.5 to 25 mg such as 0.5, 1, 2, 5, 10, 15 or 20mg. Such compositions may be administered from 1 to 6 times a day, more usually from 1 to 4 times a day, in a manner such that the daily dose is from 0.01 to 25 mg for a per kg body weight and more particularly from 0.1 to 10 mg/kg.

No toxicological effects are indicated at the aforementioned dosage ranges.

The present invention further provides a compound of formula (I) or a pharmaceutically acceptable salt thereof for use in the treatment or prophylaxis of hypertension and/or respiratory tract disorders.

The following descriptions relate to the preparation of intermediates and the following examples relate to the preparation of compounds of formula (I).

DESCRIPTION 1 trans-3-Acetoxy-6-cyano-3,4-dihydro-2,2-dimethyl-4-N-(N'-methylthioureido)-2H-1-benzopyran (D1)

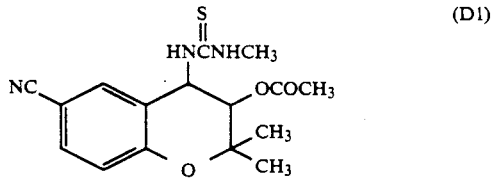

Acetic anhydride (0.53g) was added to a mixture of trans-6-cyano-3,4-dihydro-2,2-dimethyl-4-N-(N'-methylthioureido)-2H-benzopyran-3-ol (1g, as described in EP-A-126367), triethylamine (0.52g) and 4-dimethylaminopyridine (75 mg) stirred in dry dichloromethane (10 ml) at room temperature. After about 15 min a homogeneous solution was observed. After 2 h methanol (15 ml) was added and stirred for 30 min at room temperature. The solvent was evaporated in vacuo and the clear oil obtained was partitioned between ethyl acetate (50 ml) and IN hydrochloric acid (50 ml). The organic phase was then washed with water (3×50 ml) and then brine (2x30 ml), dried over anhydrous sodium sulphate and the solvent evaporated in vacuo to give a clear oil (1.3g). Trituration under ether/petrol gave the title compound as a white crystalline solid (0.57g) of melting point 194°–7° C.

60 MHz $^1$H-nmr (CDCl$_3$) δ 1.37 (s,6H); 2.13 (s,3H); 3.00 (d,J=6Hz,3H); 5.03 (d,J=9Hz,1H); 5.93 (br,dd,J=9,10Hz, 1H); 6.40 (d,J TM 9Hz,1H); 6.67-7.1 (m,2H); 7.17-7.77 (m,2H).

DESCRIPTION 2 trans-3-Acetoxy-6-cyano-3,4-dihydro-2,2-dimethyl-4-N-(N'-tert-butylthioureido)-2H-1-benzopyran (D2)

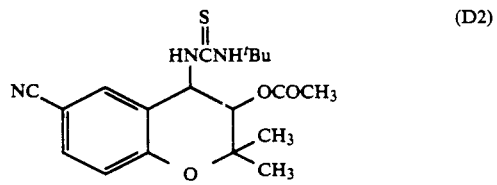

The title compound was prepared analogously to the preparation of description 1, giving a white foam.

$^1$H-nmr (CDCl$_3$) δ1.34 (s,3H); 1.49 (s,9H); 1.51 (s,3H); 3.62 (dd.J=5,10Hz,1H); 4.43–4.65 (broad signal, 1H); 5.8–6.1 (broad signal, 2H); 6.36–d6.61 (broad signal, 1H); 6.88 (d,J=8Hz, 1H); 7.43 (dd,J=2,8Hz, 1H); 7.58 (d,J=2Hz, 1H)

DESCRIPTION 3 trans-4-(2-Aminoethylamino)-6-cyano-3,4-dihydro-2,2-dimethyl-2H-1-benzopyran-3-ol (D3)

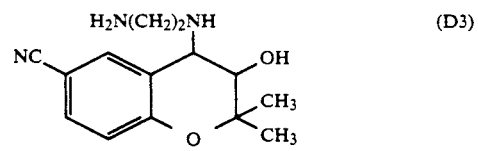

A mixture of 6-cyano-3,4-dihydro-2,2-dimethyl-3,4-epoxy-2H-1-benzopyran-3-ol (0.927g) and ethylenediamine (2.78g) was heated under reflux in ethanol (70 ml) for 16 h. The solvent was evaporated in vacuo and the residue column chromatographed (Kieselgel 60, gradient elution: 0–9% 880 ammonia-methanol) giving the title compound (0.868g) as a foam.

1H nmr (CDCl$_3$) δ 1.23 (s,3H); 1.52 (s,3H); 2.5–3.25 (m,8H); 3.55 (d,J=10Hz,1H); 3.69 (d,J=10Hz,1H); 6.82 (d,J TM 8.3Hz,1H); 7.40 (dd,J=1,8.3Hz,1H); 7.74 (d,J=1Hz,1H).

DESCRIPTION 4

N'-Cyano-N-4-(trans-6-cyano-3,4-dihydro-2,2-dimethyl-2H-1-benzopyran-3-ol)-carbamimidothioic acid methyl ester (D4)

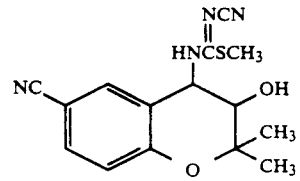

A solution of trans-4-amino-6-cyano-3,4-dihydro-2,2-dimethyl-2H-benzopyran-3-ol (3.5g) and dimethyl N-cyanodithioiminocarbonate (2.42g) in acetonitrile (5 ml) was heated in an oil bath at 90° C. under a stream of dry nitrogen for 48 h. Evaporation of the solvent gave a yellow glass which was chromatographed on silica gel (Kieselgel 60; with gradient elution; 100% chloroform-2% methanol 98% chloroform) giving the title compound as a white solid (4.8g) of m.p. 216°–8° C. (Dec.).

$^1$H-nmr (d$_6$-DMSO) δ 1.16 (s, 3H); 1.41 (s, 3H); 2.63 (s, 3H); 3.79 (dd, J=6, 10Hz, 1H); 5.07 (dd, J=9, 10Hz, 1H); 5.94 (d, J=6Hz, 1H); 6.96 (d, J=9Hz, 1H); 7.52 (d, J=2Hz, 1H); 7.64 (dd, J=2, 9Hz, 1H); 8.57 (d, J=9Hz, 1H).

DESCRIPTION 5

N'-Cyano-N-4-(trans-6-chloro-3,4-dihydro-2,2-dimethyl-2H-1-benzopyran-3-ol)-carbamimidothioic acid methyl ester (D5)

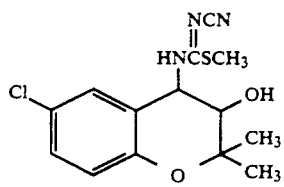

A solution of trans-4-amino-6-chloro-3,4-dihydro-2,2-dimethyl-2 ...ropy... ol (2.0g) and dimethyl-N-cyano-dithi ...iniocarbonate (1.3g) in acetonitrile (10 ml) was heated at 70°-80° C., under nitrogen, for 48h. The crystals which formed after cooling were filtered off to give the desired product (1.7g) having m.pt. 183°-5° C.

$^1$H nmr (DMSO-d$_6$) δ 1.12 (s,3H), 1.38 (s,3H), 2.63 (s,3H), 3.77 (dd, J=6, 10Hz, 1H), 5.04 (dd, J=9, 10Hz, 1H), 5.89 (d, J=6Hz, 1H), 6.82 (d, J=9Hz, 1H), 7.00 (d, J=2Hz, 1H), 7.23 (dd, J=9, 2Hz, 1H), 8.63 (d, J=9Hz, 1H).

DESCRIPTION 6

N'-Cyano-N-4-(3,4-dihydro-2,2-dimethyl-2H-pyrano[3,2-c]pyridin-3-ol)-carbamimidothioic acid, methyl ester (D6)

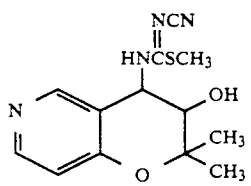

The title compound was prepared in a similar manner to that described in Description 5, to give a colourless solid having m.pt. 180°-2° C.

$^1$H nmr (DMSO-d6) δ 1.15 (s, 3H), 1.42 (s, 3H), 2.64 (s, 3H), 3.80 (dd, J=6, 10Hz, 1H), 5.10 (dd, J=9, 10Hz, 1H), 5.98 (d, J=6Hz, 1H), 6.80 (d, J TM 6Hz, 1H), 8.17 (s, 1H), 8.26 (m, 1H), 8.63 (d, J=9Hz, 1H).

DESCRIPTION 7

N'-Cyano-N-4-(trans-6-ethyl-3,4-dihydro-2,2-dimethyl-2H-benzopyran-3-ol)-carbamimidothioic acid methyl ester (D7)

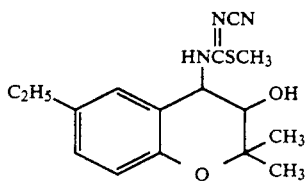

The title compound was prepared in a similar manner to that described in Description 5, to give a colourless solid having m.pt. 167°-9° C.

$^1$H nmr (DMSO-d$_6$) δ 1.10 (t, 3H), 1.12 (s, 3H), 1.37 (s, 3H), 2.5 (q, 2H), 2.62 (s, 3H), 3.74 (dd, J=6, 10 Hz, 1H), 5.06 (dd, J=9, 10Hz, 1H), 5.75 (d, J TM 6Hz, 1H), 6.70 (d, J=9Hz, 1H), 6.84 (d, J=2Hz, 1H), 7.00 (dd, J=9, 2Hz, 1H), 8.60 (d, J=10Hz, 1H).

DESCRIPTION 8 a) Trans-5-Cyano-1,1-dimethyl-3-azido-indan-2-ol

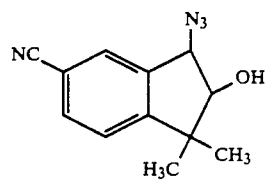

A mixture of 5-cyano-1,1-dimethyl-2,3-epoxyindane (1.34g), sodium azide (0.533g), and ammonium chloride (0.44g) in dry N,N-dimethylformamide (20 ml) was stirred and heated at 60° C., under nitrogen, for 3h. The mixture was diluted with water, and extracted with ethyl acetate. The combined organic layers were washed with water, brine, and then dried (Na$_2$SO$_4$). Removal of solvents in vacuo, followed by chromatography of the residue (Si gel, eluted with 30% EtOAc in pentane) gave the title compound as a gum (0.93g).

I.R. 2125, 2140 cm-$^1$.

Mass Spectrum: Found: M+ 228.1011; C$_{12}$H$_{12}$N$_4$O requires M+ 228.1011.

b) Trans-5-Cyano-1,1-dimethyl-3-amino-indan-2-ol

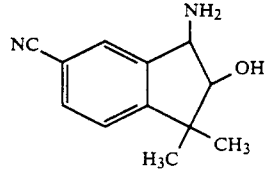

A solution of trans-5-cyano-1,1-dimethyl-3-azido-indan-2-ol (0.93g), triethylamine (1.2 ml) and 1,3-propanedithiol (0.9 ml) in dry methanol (20 ml) was stirred at room temperature for 48h. After filtration, the solution was evaporated in vacuo to give the title compound (0.79g) as a gum.

$^1$H nmr (DMSO-d$_6$) δ 1.05 (s, 3H), 1.34 (s, 3H), 2.7-3.4 (br s, 3H), 3.57 (d, J=8Hz, 1H), 4.05 (d, J=8Hz, 1H), 7.28 (d, J=8Hz, 1H), 7.65 (s, 1H).

c)

N'-Cyano-N-3-(trans-5-cyano-1,1-dimethyl-indan-2-ol)-carbamimidothioic acid methyl ester

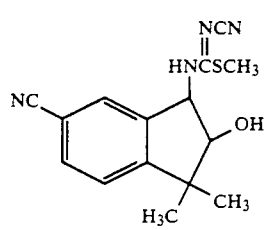

A solution of trans-5-cyano-1,1-dimethyl-3-amino-indan-2-ol (0.79g) and dimethyl-N-cyanodithioiminocarbonate (0.57g) in acetonitrile (10 ml) was heated at 70°-80° C. for 24h. The solvent was removed in vacuo, and the residue chromatographed (Si gel, eluted with 10% methanol:chloroform) to give the title compound as an off-white solid (1.05g) having m.pt. 120°-2° C.

¹H nmr (DMSO-d6) δ 1.02 (s, 3H), 1.30 (s, 3H), 2.65 (s, 3H). 4.07 (dd. J=6 10Hz. 1H). 5.30 (d. J TM 10Hz, 1H). 5.70 (d. J=6Hz. 1H). 7.4B (d. J=9Hz. 1H). 7.62 (d. J=2Hz, 1H). 7.77 (dd. J=9. 2Hz. 1H). 8.30 (s. 1H).

DESCRIPTION 9 a)
4-Chloro-6-cyano-3,4-dihydro-2,2-dimethyl-2H-1-benzopyran

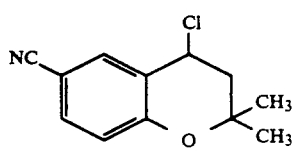

To a solution of 6-cyano-3,4-dihydro-2,2-dimethyl-2H-1-benzopyran-4-ol (U.K. Patent Application GB 2 204 868A) (2.93 g) and triethylamine (4.04 ml) in dichloromethane (100 ml) was added methanesulphonylchloride (2.24 ml) over 30 min, under an atmosphere of nitrogen. The reaction mixture was stirred for 18 h, water was added and the organic phase separated, washed with aqueous sodium hydrogencarbonate and dried over anhydrous sodium sulphate. Filtration and evaporation of the solvent in vacuo gave the title compound (3.03g) as a solid, which was used in the next step without further purification.

¹H nmr (CDCl₃) δ 1.34 (s,3H); 1.52 (s,3H); 2.26 (dd, J=9,14Hz,1H); 2.43 (dd,J TM 6,14Hz,1H); 5.18 (dd,J=6,9Hz, 1H); 6.86 (d,J TM 9Hz,1H); 7.46 (dd,J=2,9Hz,1H); 7.85 (d, J=2Hz,1H).

b)
4-Azido-6-cyano-3,4-dihydro-2,2-dimethyl-2H-1benzopyran

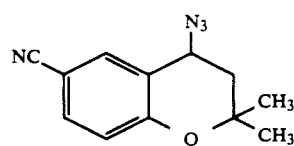

A mixture of 4-chloro-6-cyano-3,4-dihydro-2,2-dimethyl-2H-1-benzopyran(3g) and sodium azide (0.9g) in N,N-dimethylformamide (20 ml) was stirred for 3 days at room temperature. Water was added and the mixture extracted with ethyl acetate, the organic phase was separated and further washed with water, then dried over anhydrous sodium sulphate. Filtration and evaporation of the solvent in vacuo gave the title compound (3.03g) as a solid, which was used in the next step without further purification.

¹H nmr (CDCl₃) δ 1.34 (s,3H); 1.48 (s,3H); 2.01 (dd, J=9,14Hz,1H); 2.24 (dd,J TM 6,14Hz,1H); 4.59 (dd,J=6,9Hz, 1H); 6.86 (d,J=9Hz,1H); 7.47 (dd,J=2,9Hz,1H); 7.70 (d, J=2Hz,1H).

c)
4-Amino-6-cyano-3,4-dihydro-2,2-dimethyl-2H-1benzopyran

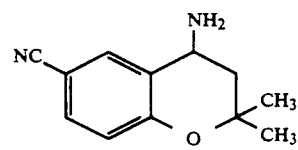

To a solution of 4-azido-6-cyano-3,4-dihydro-2,2-dimethyl-2H-1-benzopyran (0.92g) in acetone (20 ml) was added concentrated hydrochloric acid (3 ml) and zinc dust (0.6g) in portions, with vigorous stirring. After 15 min the reaction was diluted with water, filtered and the filtrate extracted with ethyl acetate. The aqueous phase was made basic with 10% (w/v) aqueous sodium hydroxide solution and further extracted with ethyl acetate. The combined organic phase was dried over anhydrous sodium sulphate, filtered and the solvent evaporated in vacuo to give the title compound (0.69g).

¹H nmr (CDCl₃) δ 1.30 (s,3H); 1.46 (s,3H); 1.68 (dd, J=12,14Hz,1H); 1.81 (brs,2H); 2.14 (dd,J=6,14Hz,1H); 4.03 (dd,J=6,12Hz.1H): 6.81 (d.J=9Hz.1H): 7.41 (dd.J=2.9Hz.1H): 7.86 (d.J=2Hz.1H).

d)
N'-Cyano-N-4-(6-cyano-3,4-dihydro-2,2-dimethyl-2H-1-benzopyran)-carbamimidothioic acid methyl ester (D9)

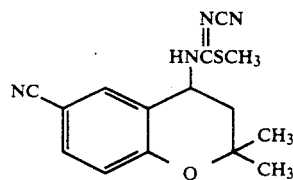

A solution of 4-amino-6-cyano-3,4-dihydro-2,2-dimethyl-2H-1-benzopyran (0.69g) and dimethyl N-cyanodithioiminocarbonate (0.245g) in acetonitrile (4 ml) was heated in an oil bath at 80° C., under an atmosphere of nitrogen for 24 h. The solvent was evaporated in vacuo to give the title compound as a solid (0.4g) after trituration under ether.

¹H nmr (CDCl₃-d₄-MeOH) δ 1.35 (s,3H); 1.50 (s,3H); 1.86 (dd,J TM 12,14Hz,1H); 2.26 (dd,J=6,14Hz,1H); 2.65 (s,3H); 4.86-5.53 (broad signal, 1H); 6.89 (d,J=9Hz, 1H); 7.40 -7.65 (m,2H).

DESCRIPTION 10

(3S,4R)-N'-Cyano-N-4-(6-cyano-3,4-dihydro-2,2-dimethyl-2H-1-benzopyran-3-ol)carbamimidothioic acid methyl ester (D10)

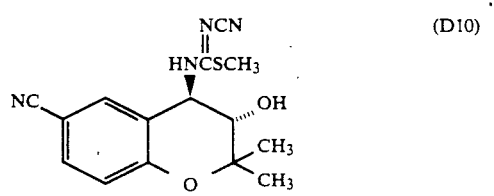

The title compound was prepared in a similar manner to that described in Description 4*, to give a colourless solid, having m.pt. 216°-8° C. (dec.).

* using resolved aminoalcohol, prepared by using the resolving agent (+)-ammonium 3-bromo-camphor-9-sulphonate.

¹H nmr (d₆1DMSO) δ 1.16 (s,3H); 1.41 (s,3H); 2.63 (s, 3H); 3.79 (dd,J=6,10Hz,1H); 5.07 (dd,J=9,10Hz, 1H); 5.96 (d,J=6Hz,1H); 6.96 (d,J=9Hz,1H); 7.52 (d,J=2Hz,1H); 7.65 (dd,J=2,9Hz,1H); 8.59 (d,J=9Hz,1H).

DESCRIPTION 11

N'-Acetyl-N-4-(trans-6-cyano-3,4-dihydro-2,2-dimethyl-2H-1-benzopyran-3-ol)-carbamimidothioic acid methyl ester (D11)

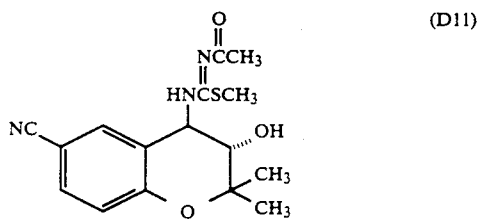

A solution of trans-4-amino-6-cyano-3,4-dihydro-2,2-dimethyl-2H-1-benzopyran-3-ol (1g) and dimethyl N-acetyldithioiminocarbonate (0.75g) in ethanol (4 ml) was allowed to stand at room temperature for 8 days. The solvent was evaporated and the resulting orange gum column chromatographed (Kieselgel 60; with gradient elution 100% chloroform - 2% methanol 98% chloroform) giving the title compound as a gum (0.24g), which was used in the next step without further purification.

EXAMPLE 1

N-trans-4-(3-Acetoxy-6-cyano-3,4-dihydro-2,2-dimethyl-2H-1-benzopyran)-N''-cyano-N'-methylguanidine (E1)

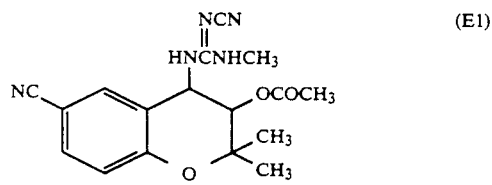

Phosgene in toluene (1.93 M, 1.5 ml) was added to a stirred solution of trans-3-acetoxy-6-cyano-3,4-dihydro-2,2-dimethyl-4-N-(N'-methylthioureido)-2H-benzopyran (D1) (0.57 g) in dry tetrahydrofuran (7 ml) at 0° C. under an atmosphere of nitrogen. The reaction vessel was sealed and allowed to warm to room temperature and stirred for 18 h. The solvent was evaporated in vacuo and the residue dissolved in dry tetrahydrofuran (7 ml), cooled to ice-bath temperature and N,N-diisopropylethylamine (0.7 ml) added with stirring. Cyanamide (90 mg) was then added and the mixture was stirred for 3 days at room temperature. The solvent was evaporated in vacuo and the residue partitioned between ethyl acetate (25 ml) and 0.5N hydrochloric acid (20 ml). The aqueous phase was further extracted with ethyl acetate (20 ml), and the combined organic phase washed with water (3×25 ml), dilute sodium bicarbonate solution (0.5%, 20 ml) and then brine (2×25 ml), dried over anhydrous magnesium sulphate and evaporated in vacuo to give a crude white solid. Column chromatography (Kieselgel 60, gradient elution: 0–1% methanol-chloroform) gave an oil (180 mg) which was crystallised from chloroform-ether to give the title compound (120 mg), of melting point 244°-5° C. (dec.).

270 MHz ¹H nmr (d₆-DMSO) δ 1.31 (s,3H); 1.40 (s,3H); 2.11 (s,3H); 2.79 (d,J=5Hz,3H); 5.13-5.27 (m,2H); 6.92 (d,J=8Hz,1H); 7.05 (br.q,J=5Hz,1H); 7.20 (br.d,J=9Hz, 1H); 7.47-7.56 (m,2H).

Mass spectrum: found M⁺ 341.1489, C₁₇H₁₉N₅O₃ requires 341.1488.

EXAMPLE 2

N''-Cyano-N-trans-4-(6-cyano-3,4-dihydro-2,2-dimethyl-2H-1-benzopyran-3-ol)-N'-methylguanidine (E2)

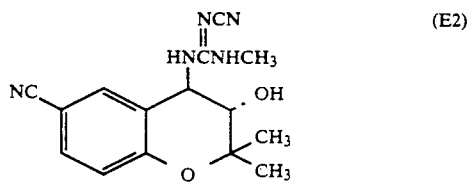

Potassium carbonate (17 mg) and N-trans-4-(3-acetoxy-6-cyano-3,4-dihydro2,2-dimethyl-2H-benzopyran)-N''-cyano-N'-methylguanidine (E1) (170 mg) were stirred in methanol (17 ml) at room temperature for 90 min. The solvent was evaporated in vacuo and the residue partitioned between chloroform (30 ml) and water (20 ml). The aqueous phase was further extracted with chloroform (25 ml). The combined organic phase was then washed with brine and dried over anhydrous sodium sulphate. Evaporation of the solvent in vacuo gave a crude oil (140 mg) which was crystallised from ethyl acetate-diisopropyl ether to give the title compound (100 mg) of melting point 225°-7° C.

270 MHz ¹H-nmr (d₆-DMSO) δ 1.16 (s,3H); 1.41 (s,3H); 2.76 (d,J ᴛᴍ 4Hz,3H); 3.72 (dd,J=6,10Hz,1H); 4.80 (br.dd, J=8,10Hz,1H); 5.81 (d,J=6Hz,1H); 6.93 (d,J=9Hz,1H); 7.2-7.32 (m,2H); 7.49 (d,J=2Hz,1H); 7.62 (dd,J ᴛᴍ 9,2Hz,1H).

Mass spectrum: found M⁺ 299.1387, C₁₅H₁₇N₅O₂ requires 299.1382.

EXAMPLE 3

N-trans-4-(3-Acetoxy-6-cyano-3,4-dihydro-2,2-dimethyl-2H-1-benzopyran-N''-cyano-N'-tert-butylguanidine (E3)

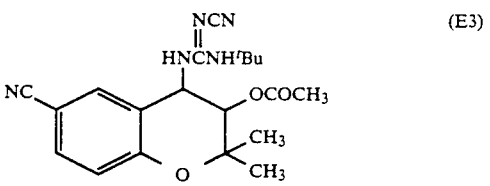

The title compound was prepared from D2 analogously to the preparation of the N'-methylguanidine of Example 1, giving a white crystalline solid m.p. 216°-218° C.

1H nmr (CDCl₃) δ 1.41 (s,3H); 1.43 (s,12H); 2.15 (s,3H); 4.8-5.2 (brm,3H); 5.71 (br.s,1H); 6.94 (d,J=9Hz,1H); 7.51 (dd,J=2,9Hz,1H); 7.56 (d,J=2Hz,1H).

EXAMPLE 4

N''-Cyano-N-trans-4-(6-cyano-3,4-dihydro-2,2-dimethyl-2H-1-benzopyran-3-ol)-N'-tert-butylguanidine (E4)

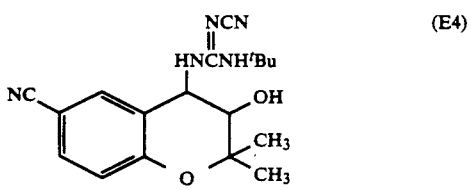

The title compound was prepared from E3 analogously to the preparation of the N'-methylguanidine of Example 2, giving a white crystalline compound of m.p. 198°-201° C.

1H nmr (CDCl₃) δ 1.24 (s,3H); 1.37 (s,9H); 1.49 (s,3H); 3.71 (dd,J=6,10Hz,1H); 4.6 (broad signal,1H); 5.06 (broad signal,1H); 5.73 (broad signal,1H); 6.21 (broad signal,1H); 6.86 (d,J=8Hz,1H); 7.46 (dd,J=2,8Hz,1H); 7.67 (d,J TM 2Hz,1H).

EXAMPLE 5 trans-6-Cyano-4-[2-(N-cyanoimino)imidazolidin-1-yl]-3,4-dihydro-2,2-dimethyl-2H-1-benzopyran-3-ol (E5)

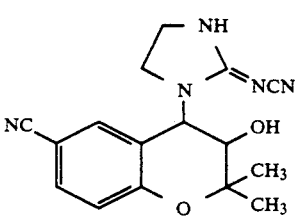

A mixture of trans-4-(2-aminoethylamino)-6-cyano-3,4-dihydro-2,2-dimethyl-2H-1-benzopyran-3-ol (D3) (0.39g) and dimethyl N-cyanodithioiminocarbonate (0.158g) was heated under reflux in toluene (30 ml) for 71 h. The solvent was evaporated in vacuo, and the residue column chromatographed (Kieselgel 60, gradient elution: 2-7% methanol-chloroform) giving the title compound as a white solid (0.33g). Recrystallisation from ethyl acetate-ether gave a sample of m.p. 257°-260° C.

¹H nmr (CDCl₃-d₆ DMSO) δ 1.01 (s,3H); 1.26 (s,3H); 2.95 (m,1H); 3.32-3.47 (m,4H); 4.76 (d,J=10.5Hz,1H); 5.21 (d,J=5.8Hz, disappears with D₂O,1H); 6.62 (d,J=8.5Hz, 1H); 7.05 (m,1H); 7.19 (m,1H); 7.49 (s, disappears with D₂O,1H).

Anal. Found C,61.79; H,5.56; N,22.12. C₁₆H₁₇N₅O₂ requires C,61.72; H,5.51; N,22.50%.

EXAMPLE 6

N'-Cyano-N-4-(trans-6-cyano-3,4-dihydro-2,2-dimethyl-2H-1-benzopyran-3-ol)guanidine (E6)

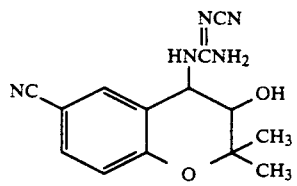

A solution of N'-cyano-4-(trans-6-cyano-3,4-dihydro-2,2-dimethyl-2H-benzopyran-3-ol)-carbamimidothioic acid methyl ester (D4) (0.6g), aqueous ammonia solution (sp.gr.0.88; 10 ml) and pyridine (4 ml) was allowed to stand at room temperature for 90 h. The solvent was evaporated in vacuo and the residual oil dissolved in ethyl acetate (30 ml) and evaporated in vacuo. The residue was again dissolved in ethyl acetate (30 ml) and evaporated in vacuo. Recrystallization from ethanol-isopropanol-ethyl acetate gave the title compound as a white solid (0.34g) of m.p. 248°-50° C.

'H-nmr (d₆-DMSO) δ 1.27 (s, 3H); 1.50 (s, 3H); 3.68 (dd, J=6, 10Hz, 1H); 4.60-4.95 (broad signal, 1H); 5.87 (br.s. 1H); 6.98 (br.s, 2H); 7.03 (d, J=9Hz, 1H); 7.36 (br.s, 1H); 7.56 (d, J=2Hz, 1H); 7.72 (dd, J=2, 9Hz, 1H).

Analysis: Found C,58.79; H,5.34; N,24.35%. C₁₄H₁₅N₅O₂ requires, C,58.94; H,5.30; N,24.55%.

EXAMPLE 7

N''-Cyano-N-trans-4-(6-chloro-3,4-dihydro-2,2-dimethyl-2H-1-benzopyran-3-ol)-N'-methylguanidine (E7)

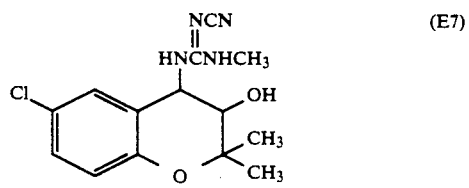

A solution of N'-cyano-N-4-(trans-6-chloro-3,4-dihydro-2,2-dimethyl-2H-benzopyran-3-ol)-carbamimidothioic acid methyl ester (D5) (325 mg), in 10 ml of 33% methylamine in IMS solution was allowed to stand at room temperature for 24h. Solvents were removed in vacuo, and the residue recrystallised from ethyl acetate —60°-80° C. petrol as an off-white solid (240 mg) having m.pt. 197°-9° C.

¹H nmr (DMSO-d₆) δ 1.13 (s, 3H), 1.38 (s, 3H), 2.74 (d, J TM 4Hz, 3H), 3.68 (dd, J TM 6, 10Hz, 1H), 4.75 (dd, J=9, 10Hz, 1H), 5.72 (d, J=6Hz, 1H), 6.77 (d, J=9Hz, 1H), 7.00 (d, J=2Hz, 1H), 7.18 (dd, J=9, 2Hz, 1H), 7.20-7.30 (m, 2H).

EXAMPLE 8

N''-Cyano-N-trans-4-(3,4-dihydro-2,2-dimethyl-2H-pyrano[3,2-c]pyridin-3-ol)-N'-methylguanidine (E8)

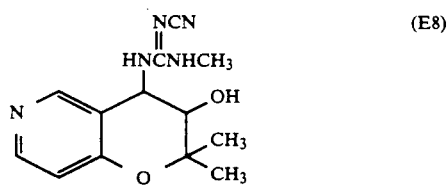

A similar procedure to that described in Example 7, gave the title compound from D6, as colourless crystals, having m.pt. 284°-6° C. (MeOH/EtOAc).

¹H nmr (DMSO-d₆) δ 1.15 (s, 3H), 1.40 (s, 3H), 2.74 (d, J=4Hz, 3H), 3.71 (dd, J=6, 10Hz, 1H), 4.82 (dd, J=9, 10Hz, 1H), 5.82 (d, J=6Hz, 1H), 6.77 (d, J=9Hz, 1H), 7.20-7.30 (m, 2H), 8.18 (d, J=2Hz, 1H), 8.22 (dd, J=9, 2Hz, 1H).

EXAMPLE 9

N''-Cyano-N-trans-4-(6-ethyl-3,4-dihydro-2,2-dimethyl-2H-1-benzopyran-3-ol)-N'-methylguanidine (E9)

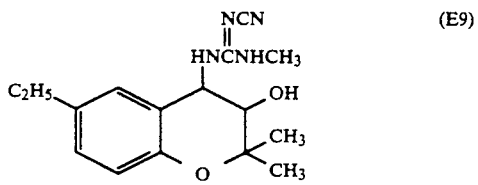
(E9)

A similar procedure to that described in Example 7, gave the title compound from D7, as colourless crystals having m.pt. 208°-9° C. (EtOAc —60°-80° petrol).

$^1$H nmr (DMSO-d$_6$) δ 1.10 (s, 3H), 1.12 (t, 3H), 1.35 (s, 3H), 2.50 (q, 2H), 2.74 (d, J TM 4Hz, 3H), 3.57 (dd, J TM 6, 10Hz, 1H), 4.78 (dd, J=9,10Hz, 1H), 5.58 (d, J=6Hz, 1H), 6.65 (d, J=9Hz, 1H), 6.90 (d, J=2Hz, 1H), 6.98 (dd, J=9, 2Hz, 1H), 7.10-7.24 (m, 2H).

EXAMPLE 10

N''-Cyano-N-trans-3-(5-cyano-1,1-dimethyl-indan-2-ol)-N'-methylguanidine (E10)

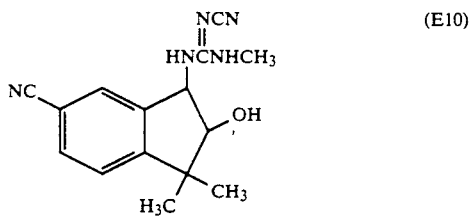
(E10)

A similar procedure to that described in Example 7, gave the title compound from F8 as off-white crystals, having m.pt. 244°-6° C. (EtOAc-MeOH).

$^1$H nmr (DMSO-d$_6$) δ 1.02 (s, 3H), 1.30 (s, 3H), 2.75 (d, J=4Hz, 3H), 4.00 (dd, J=6, 10Hz, 1H), 5.03 (dd, J TM 9, 10Hz, 1H), 5.60 (d, J=6Hz, 1H), 7.20-7.30 (m, 2H), 7.45 (d, J=9Hz,1H), 7.50 (d, J=2Hz, 1H), 7.74 (dd, J=9, 2Hz, 1H).

EXAMPLE 11

N'''-Cyano-N-(6-cyano-3,4-dihydro-2,2-dimethyl-2H-1-benzopyran)-N'-methylguanidine (E11)

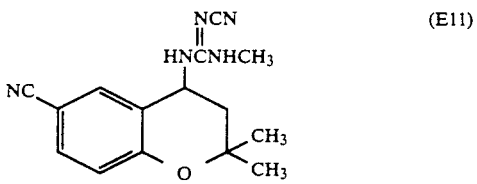
(E11)

A similar procedure to that described in Example 7, gave the title compound from D9 as colourless crystals, having m.pt. 230°-3° C. (EtOAc/Pentane).

$^1$H nmr (d$_6$-DMSO) δ 1.27 (s,3H); 1.41 (s,3H); 1.88 (dd, J=12,14Hz,1H); 2.11 (dd,J TM 6,14Hz,1H); 2.74 (d,J=5Hz, 3H); 4.98-5.16 (m,1H); 6.91 (d,J TM 9Hz,1H); 7.20-7.48 (m,2H); 7.55-7.67 (m,2H).

EXAMPLE 12

N-trans-4-(3-Acetoxy-6-cyano-3,4-dihydro-2,2-dimethyl-2H-1-benzopyran)-N'-methyl-N'''-sulphamoyl-guanidine (E12)

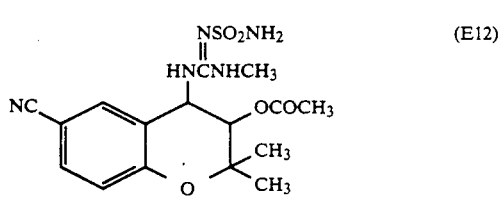
(E12)

Phosgene in toluene (1.93 M. 1.5 ml) was added to a stirred solution of trans-3-acetoxy-6-cyano-3,4-dihydro-2,2-dimethyl-4-N-(N'-methylthioureido)-2H-benzopyran (D1) (0.57 g) in dry tetrahydrofuran (7 ml) at 0° C. under an atmosphere of nitrogen. The reaction vessel was sealed and allowed to warm to room temperature and stirred for 72 h. The solvent was evaporated in vacuo and the residue dissolved in dry tetrahydrofuran (7 ml), cooled to ice-bath temperature and N,N-diisopropylethylamine (1.3 ml) added with stirring. After 30 min the mixture was allowed to warm to room temperature and then stirred for 1 h, under an atmosphere of nitrogen. The solvent was evaporated in vacuo, the residue triturated with a solution of diethylether and diisopropylether (1:1), and evaporation of the solvents in vacuo gave a brown gum, which was dissolved in acetonitrile (5 ml). Sulfamide (0.5 g) was added and the reaction mixture allowed to stand at room temperature for 10 days. The solvent was evaporated in vacuo and the residue partitioned between chloroform and water (pH adjusted to 7 with dilute hydrochloric acid). The organic phase was further washed with water then brine, dried over anhydrous sodium sulphate, filtered and the solvent evaporated in vacuo to give a brown oil. Column chromatography (Kieselgel 60, eluting with chloroform-methanol 45:1) followed by chromatography (neutral alumma, gradient elution 0-5% methanol-chloroform) gave the title compound as a colourless oil (90 mg).

$^1$H nmr (CDCl$_3$) δ 1.37 (s,3H); 1.43 (s,3H); 2.16 (s,3H); 2.88 (broad signal, 3H, collapses to singlet on addition of d$_4$-MeOH); 4.65 (brs, 2H, disappears on addition of d$_4$-MeOH); 5.08 (broad signal, 2H, collapses to d,J=10Hz,1H at δ 5.18 on addition of d$_4$-MeOH); 5.37 (broad signal, 1H); 6.90 (d,J=9Hz,1H); 7.22 (brs,1H, disappears on addition of d$_4$-MeOH); 7.47 (dd,J=2,9Hz, 1H); 7.66 (d,J=2Hz,1H).

EXAMPLE 13

N-trans-4-(6-Cyano-3,4-dihydro-2,2-dimethyl-2H-benzopyran-3-ol)-N'-methyl-N''-sulphamovl-guanidine (E13)

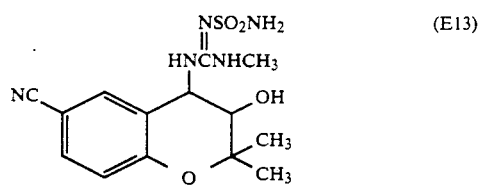
(E13)

The title compound was prepared from E'2 analogously to the preparation of the N'''-cyano-N'-methyl guanidine of Example 2, giving a white crystalline solid of melting point 160°-5° C. (EtOAc-diisopropylether).

¹H nmr (d₆-acetone) δ 1.26 (s,3H); 1.47 (s,3H); 2.95 (brs,3H); 3.81 (dd,J=6,10Hz,1H); 5.16 (brs,1H);: 5.37 (brs,1H); 5.64 (s,2H); 6.46 (brs,1H); 6.91 (d,J=9Hz, 1H); 7.21 (brs,1H); 7.54 (dd,J=2,9Hz,1H); 7.77 (brs, 1H).

EXAMPLE 14

N''-Carboxamido-N-trans-4-(6-cyano-3,4-dihydro-2,2-dimethYl-2H-1-benzopyran-3-ol)-N'-methyl-guanidine (E14)

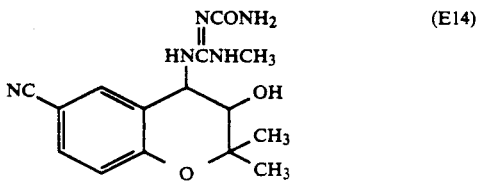

N'''-Cyano-N-trans-4-(6-cyano-3,4-dihydro-2,2-dimethyl-2H-benzopyran-3-ol)-N'-methylguanidine (E2) (0.3g) was dissolved in warm ethanol (20 ml) and 1 N hydrochloric acid (5 ml) added the solution heated at about 45° C. for 30 min. The solvent was evaporated in vacuo and the residue partitioned between chloroform and water, the aqueous phase was neutralized with saturated sodium carbonate solution and the organic phase separated, washed with brine then dried over anhydrous sodium sulphate. Filtration and evaporation of the solvent gave a gum which was chromatographed (chromatotron-Kieselgel 60:gradient elutions 0–10% methanol-chloroform) to give the title compound as a white foam (0.145g).

¹H nmr (d₆-DMSO) δ 1.16 (s,3H); 1.40 (s,3H); 2.76 (d, J=5Hz,3H, collapses to a singlet on addition of D₂O); 3.51-3.78 (broad signal, 1H); 4.90-5.30 (broad signal, 1H); 5.44-5.97 (broad signal, 2H, disappears on addition of D₂O); 6.06 (brs,1H, disappears on addition of D₂O); 6.50-6.80 (broad signal, 1H, disappears on addition of D₂O); 6.92 (d,J TM 10Hz,1H); 7.51-7.68 (m,2H); 9.42-9.70 (broad signal, 1H, disappears on addition of D₂O).

EXAMPLE 15

(3S,4R)-N''-Cyano-N-4-(6-cyano-3,4-dihydro-2,2-dimethyl-2H-1-benzopyran-3-ol)-N'-methylguanidine (E15)

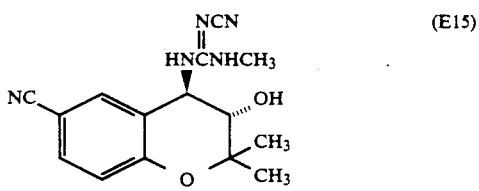

A Similar procedure to that described in Example 7, gave the title compound from D10 as a white microcrystalline solid having m.pt 223°-4° C. (EtOAc-pentane). [α]_D^{20} (c=1, MeOH) = −61.9°.

¹H nmr (d₆-DMSO) δ 1.15 (s,3H); 1.41 (s,3H); 2.75 (d,J=4Hz,3H); 3.72 (dd.J=6 10Hz,1H); 4 79 (dd,J=8,10Hz, 1H);: 5.81 (d,J=6Hz,1H); 6.93 (d,J=9Hz,1H); 7.18-7.35 (m,2H); 7.48 (d,J=2Hz,1H); 7.62 (dd,J TM 2,9Hz,1H).

EXAMPLE 16

N'''-Cyano-N-4-(6-cyano-2.2-dimethyl-2H-1-benzopyran)-N'-methylguanidine (E16)

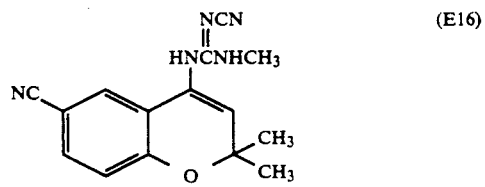

A solution of N'''-cyano-N-trans-4-(6-cyano-3,4-dihydro-2,2-dimethyl-2H-1-benzopyran-3-ol)-N'-methylguanidine (E2) (0.5g) and sodium hydride (80% dispersion in mineral oil, 58 mg) in dry tetrahydrofuran (25 ml) was heated under reflux for 17h, under an atmosphere of nitrogen. Toluene (25 ml) was added and the mixture further heated under reflux for 24h, under an atmosphere of nitrogen. After cooling, the mixture was filtered and the residue washed thoroughly with ethyl acetate. The filtrate was evaporated to dryness in vacuo to give a yellow solid (0.45g), a sample of which (0.1g) was column chromatographed (Kieselgel 60, elution with 2% methanol-98% chloroform) to give the title product as a lemon coloured solid (58 mg). Recrystallization from chloroform gave a colourless microcrystalline solid having m.p. 249°-252° C. (dec.).

¹H nmr (d₆-DMSO) δ 1.39 (s,6H); 2.93 (s,3H); 5.36 (s,1H); 7.01 (d,J=9Hz,1H); 7.68 (dd,J=2,9Hz,1H); 7.84 (d,J=2Hz,1H); 9.22 (s,1H); 11.79 (brs,1H).

EXAMPLE 17

N''-Acetyl-N-4-(trans-6-cyano-3,4-dihydro-2,2-dimethyl -2H-1-benzopyran-3-ol)-N'-methylcuanidine (E17)

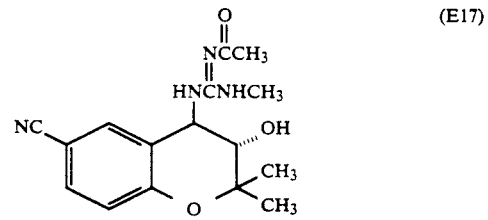

Methylamine in IMS solution (2 ml) was added to a solution of N'-acetyl-N-4-(trans-6-cyano-3,4-dihydro-2,2-dimethyl-2H-1-benzopyran-3-ol)carbamimidothioic acid methyl ester (0.22g) in ethanol (3 ml). After 26h the solvent was evaporated in vacuo, and the residue dissolved in ethyl acetate. The organic solution was washed successively with water, dilute hydrochloric acid, water and brine, then dried over anhydrous sodium sulphate. The solution was filtered, and evaporated in vacuo. The resulting gum was chromatotroned (silica gel: gradient elution 0–2% methanol in chloroform) giving a fraction containing the title compound as a white solid (63 mg) having m.pt 166°-7° C.

¹H nmr (d₆-DMSO) δ 1.29 (s, 3H); 1.51 (s, 3H); 2.10 (s, 3H); 2.94 (s, 3H); 3.72 (d, J TM 10Hz, 1H); 4.30-5.30 (broad signal, 1H); 5.13 (d, J=10Hz,1H); 6.93 (d, J=9Hz, 1H); 7.49 (dd, J=2, 9Hz, 1H); 7.63 (d, J=2Hz, 1H); 10.28 (brs, 1H).

PHARMACOLOGICAL DATA

1. Antihypertensive Activity

Systolic blood pressures were recorded by a modification of the tail cuff method described by I. M. Claxton, M. G. Palfreyman, R. H. Poyser, R. L. Whiting, European Journal of Pharmacology, 37, 179 (1976). A W+W BP recorder, model 8005 was used to display pulses. Prior to all measurements rats were placed in a heated environment (33.5±0.5° C.) before transfer to a restraining cage. Each determination of blood pressure was the mean of at least 5 readings. Spontaneously hypertensive rats (ages 12-18 weeks) with systolic blood pressures >180 mmHg were considered hypertensive.

The compounds of Examples 2, 6, 8 and 10 lowered blood pressure in the range 20-30% at a dose of 1mg/kg po.

2 Bronchodilator Activity

Male guinea pigs (300-600g) were stunned by a blow to the head and bled from the carotid artery. The trachea was exposed, dissected free of connective tissue, and transferred to oxygenated Krebs solution at 37° C. Next, spirals (2 per trachea) were prepared by cutting the whole trachea spirally along its longitudinal axis and then dividing this spiral lengthwise. Each preparation was mounted, using silk thread, in a 10ml organ bath filled with Krebs solution at 37° C. and bubbled with 5% $CO_2$ with $O_2$. The resting tension of the preparations was set at 2g and changes in muscle tension were monitored isometrically by means of a UFI (2oz) force and displacement transducer (Ormed Ltd) connected to a Linseis pen recorder. All preparations were allowed to equilibrate for 60 minutes. During this equilibration period the preparations were washed by upward displacement at 15 minute intervals and, if necessary, the resting tension was readjusted to 2g using a mechanical micromanipulator system.

Once a steady resting tension had been obtained, the preparations were dosed simultaneously with the test compound ($10^{-8}-2\times10^{-5}$M), and finally a maximum relaxation achieved by addition of $10^{-3}$M isoprenaline. The fall in tension evoked by the test compound was expressed as a percentage of the total relaxation evoked in the presence of $10^{-3}$ isoprenaline. Appropriate concentration-relaxation curves were then constructed and values for potency ($IC_{50}$) were obtained.

[The composition of Krebs solution is: sodium chloride 118.07mM, sodium hydrogen carbonate 26.19mM, potassium chloride 4.68mM, potassium orthophosphate 1.18mM, magnesium sulphate septahydrate 1.8mM and calcium chloride 2.52mM;pH ca. 7.45.]

The compound of Example 2 gave an $IC_{50}$ value of 5.5μmol.

We claim:

1. A compound of formula (I) or a pharmaceutically acceptable salt thereof:

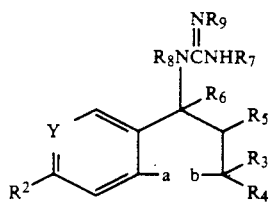
(I)

wherein
a and b together form an —O— linkage;
Y is C-$R_1$ wherein
either $R_2$ is hydrogen and $R_1$ is $C_{1-6}$ alkyl, nitro, cyano, halo, $CF_3$, formyl, aldoxime, $CF_{30}$, $NO_2$-CH=CH—, NC—CH=CH—; a group $R_xX$— wherein $R_x$ is $C_{1-6}$ alkyl, aryl or heteroaryl either of which may be optionally substituted by one, two or three of $C_{1-4}$ alkyl, $C_{1-4}$ alkoxy, nitro, halo, $CF_3$ and cyano; and X is C=O, O.C=O C=O.O, CHOH, SO, $SO_2$, O.SO, $O.SO_2$, CONH, O.CONH, C=S, O.C=S, C=S.O, CH.SH, SONH, $SO_2$NH, O.-SONH, $O.SO_2$NH, CO—CH=CH, C=NHOH, C=$NNH_2$; or a group $R_yR_zNZ$— wherein $R_y$ and $R_z$ are independently hydrogen or $C_{1-6}$ alkyl and Z is C=O, SO or $SO_2$; or
one of $R_1$ and $R_2$ is nitro, cyano or $C_{1-3}$ alkylcarbonyl and the other is a different group selected from nitro, cyano, halo, $C_{1-3}$ alkylcarbonyl, methoxy c, amino optionally substituted by one or two $C_{1.}$, alkyl or by $C_{2-7}$ alkanoyl;
one of $R_3$ and $R_4$ is hydrogen or $C_{1-4}$ alkyl and the other is $C_{1-4}$ alkyl;
$R_5$ is hydrogen, hydroxy, $C_{1-6}$ alkoxy or $C_{1-7}$ acyloxy;
$R_6$ is hydrogen; or
$R_5$ and $R_6$ together are a bond;
$R_7$ is hydrogen, $C_{1-6}$ alkyl, $C_{3-6}$ cycloalkyl, $C_{2-6}$ alkenyl or $C_{2-6}$ alkynyl; and
$R_8$ is hydrogen $C_{1-6}$ alkyl; or
$R_9$ is CN; and
the $R_8N(NR_9)NHR_7$ moiety is trans to the $R_5$ group when $R_5$ is hydroxy, $C_{1-6}$ alkoxy or $C_{1-7}$ acyloxy.

2. A compound according to claim 1, wherein $R_3$ and $R_4$ are both methyl groups.

3. A compound according to claim 1 of formula (II):

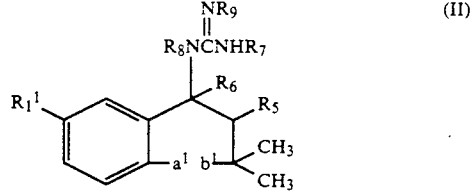
(II)

wherein $R_1^1$ is nitro, cyano, $CF_3$, methyl, ethyl, isopropyl or acetyl, $a^1$ and $b^1$ together form an —O— linkage or a bond; and $R_5$ to $R_9$ are as defined in claim 1.

4. A compound according to claim 3 wherein $R_1^1$ is cyano.

5. A compound according to claim 1 wherein $R_5$ is hydroxy or $R_5$ and $R_6$ together are a bond.

6. A compound according to claim 1, wherein $R_7$ and $R_8$ are independently selected from hydrogen or methyl.

7. A compound according to claim 1 wherein $R_9$ is cyano.

8. A compound selected from the group consisting of:
N-trans-4-(3-acetoxy-6-cyano-3,4-dihydro-2,2-dimethyl-2H-1-benzopyran)-N''-cyano-N'-methylguanidine,
N''-cyano-N-trans-4-(6-cyano-3,4-dihydro-2,2-dimethyl-2H-1-benzopyran-3-ol)-N'-methylguanidine,
N-trans-4-(3-acetoxy-6-cyano-3,4-dihydro-2,2-dimethyl-2H-1-benzopyran-N''-cyano-N'-tert-butylguanidine, N'''-cyano-N-trans-4-(6-cyano-3,4-dihydro-2,2-dimethyl-2H-1-benzopyran-3-ol)-N'-tert-butyl-guanidine, trans-6-cyano-4-[2-(N-cyanoimino)imidazolidin-1-yl]3,4-dihydro-2,2-dimethyl-2H-1-benzopyran-3-ol, N'-cyano-N-4-(trans-6-cyano-3,4-dihydro-2,2-dimethyl-2H-1-benzopyran-3-ol)guanidine, N''-cyano-N-trans-4-(6-chloro-3,4-dihydro-2,2-dimethyl-2H-1-benzopyran-3-ol)-N'-methylguanidine, N''-cyano-N-trans-4-(3,4-dihydro-2,2-dimethyl-2H-pyrano[3,2-c]pyridin-3-ol)-N'-methylguanidine, N''-cyano-N-trans-4-(6-ethyl-3,4-dihydro-2,2-dimethyl-2H-1-benzopyran-3-ol)-N'-methylguanidine, N''-cyano-N-trans-3-(5-cyano-1,1-dimethyl-indan-2-ol)-N'-methylguanidine, N''-cyano-N-(6-cyano-3,4-dihydro-2,2-dimethyl-2H-1-benzopyran)-N'-methylguanidine, N-trans-4-(3-acetoxy-6-cyano-3,4-dihydro-2,2-dimethyl-2H-1-benzopyran)-N'-methyl-N''-sulphamoyl-guanidine, N-trans-4-(6-cyano-3,4-dihydro-2,2-dimethyl-2H-benzopyran-3-ol)-N'-methyl-N''-sulphamoyl-guanidine, N'''-carboxamido-N-trans-4-(6-cyano-3,4-dihydro-2,2-dimethyl-2H-1-benzopyran-3-ol)-N'-methyl-guanidine, (3S,4R)-N'''-cyano-N-4-(6-cyano-3,4-dihydro-2,2-dimethyl-2H-1-benzopyran-3-ol)-N'-methylguanidine, N''-cyano-N-4-(6-cyano-2,2-dimethyl-2H-1-benzopyran)-N'-methylguanidine and N'''-acetyl-N-4-(trans-6-cyano-3,4-dihydro-2,2-dimethyl-2H-1-benzopyran-3-ol)-N'-methylguanidine.

9. An antihypertensive and/or bronchodilator pharmaceutical composition comprising an effective amount of a compound according to claim 1 and a pharmaceutically acceptable carrier.

10. A method of treatment of hypertension and/or respiratory tract disorders in mammals which comprises the administration to the mammal of an effective amount of a compound according to claim 1.

11. A bronchodilator pharmaceutical composition comprising an effective amount of a compound according to claim 1 and a pharmaceutically acceptable carrier.

12. A method of treatment of respiratory tract disorders in mammals which comprises the administration to the mammal of an effective amount of a compound according to claim 1.

* * * * *